United States Patent
Kanomata et al.

(10) Patent No.: US 9,267,887 B2
(45) Date of Patent: Feb. 23, 2016

(54) HIGH-PRESSURE FLUORESCENCE FLOW CELL, FLOW CELL ASSEMBLY, FLUORESCENCE DETECTOR, AND SUPERCRITICAL FLUID CHROMATOGRAPH

(71) Applicant: JASCO Corporation, Hachioji-shi, Tokyo (JP)

(72) Inventors: Takeshi Kanomata, Hachioji (JP); Yoshiteru Horikawa, Hachioji (JP); Shinichi Kikuchi, Hachioji (JP)

(73) Assignee: JASCO Corporation, Tokyo (JP)

( * ) Notice: Subject to any disclaimer, the term of this patent is extended or adjusted under 35 U.S.C. 154(b) by 445 days.

(21) Appl. No.: 13/707,976

(22) Filed: Dec. 7, 2012

(65) Prior Publication Data
US 2013/0161243 A1 Jun. 27, 2013

(30) Foreign Application Priority Data
Dec. 9, 2011 (JP) ................. 2011-270374

(51) Int. Cl.
| | |
|---|---|
| *G01N 1/10* | (2006.01) |
| *G01N 21/64* | (2006.01) |
| *G01N 30/74* | (2006.01) |
| *G01N 21/03* | (2006.01) |
| *B01D 15/40* | (2006.01) |

(52) U.S. Cl.
CPC ............ *G01N 21/64* (2013.01); *G01N 21/0317* (2013.01); *G01N 21/645* (2013.01); (Continued)

(58) Field of Classification Search
CPC ............... B01D 15/40; G01N 21/0317; G01N 2021/0346; G01N 2021/0378; G01N 2021/0382; G01N 2021/6417; G01N 2021/6467; G01N 2021/6482; G01N 2021/6484; G01N 21/64; G01N 21/645; G01N 30/74
See application file for complete search history.

(56) References Cited

U.S. PATENT DOCUMENTS

| | | | |
|---|---|---|---|
| 4,375,163 A | 3/1983 | Yang | |
| 4,601,582 A * | 7/1986 | Casey, Jr. ................ | F21V 19/04 250/373 |

(Continued)

FOREIGN PATENT DOCUMENTS

| | | |
|---|---|---|
| JP | 60-207038 | 10/1985 |
| JP | 0178935 | 5/1989 |

(Continued)

OTHER PUBLICATIONS

Extended European Search Report, Application No. EP 12196334.2 dated Dec. 18, 2013, 9 pages.
(Continued)

*Primary Examiner* — Kara E Geisel
*Assistant Examiner* — Shawn DeCenzo
(74) *Attorney, Agent, or Firm* — Rankin, Hill & Clark LLP

(57) ABSTRACT

A high-pressure fluorescence flow cell comprises a cell body made of a light-transmissive material, wherein the cell body is penetrated by a straight-line flow path for a high-pressure fluid, wherein the flow path is formed with a cross section of 0.1 mm² to 5 mm², both inclusive, orthogonal to its longitudinal direction, wherein the ratio t/d of the wall thickness t (mm) to the width d (mm) of the flow path satisfies formula (1) below, $$\frac{t}{d} \geq \frac{1}{2} \times \left[ \sqrt{\frac{\sigma+P}{\sigma-P}} - 1 \right] \times 1.5 \quad (1)$$

where σ indicates the tensile stress (MPa) of the material of the cell body, and P indicates the withstand pressure (MPa) of the cell body.

7 Claims, 15 Drawing Sheets

(52) U.S. Cl.
CPC .............. *G01N 30/74* (2013.01); *B01D 15/40* (2013.01); *G01N 2021/0346* (2013.01); *G01N 2021/0378* (2013.01); *G01N 2021/0382* (2013.01); *G01N 2021/6417* (2013.01); *G01N 2021/6467* (2013.01); *G01N 2021/6482* (2013.01); *G01N 2021/6484* (2013.01)

(56) References Cited

U.S. PATENT DOCUMENTS

| | | |
|---|---|---|
| 4,867,559 A | 9/1989 | Bach |
| 5,057,216 A | 10/1991 | Chervet |
| 5,606,412 A | 2/1997 | Saito et al. |
| 2008/0223154 A1 | 9/2008 | Kondo et al. |
| 2010/0012330 A1* | 1/2010 | Ezell et al. ................ 166/387 |
| 2011/0042581 A1 | 2/2011 | Gunji |

FOREIGN PATENT DOCUMENTS

| | | |
|---|---|---|
| JP | 0320643 | 1/1991 |
| JP | 2006-300961 | 11/2006 |

OTHER PUBLICATIONS

Patent Abstracts of Japan, Publication No. 60-207038, 1 page.
Patent Abstracts of Japan and Machine Translation, Publication No. 2006-300961, 17 pages.

* cited by examiner

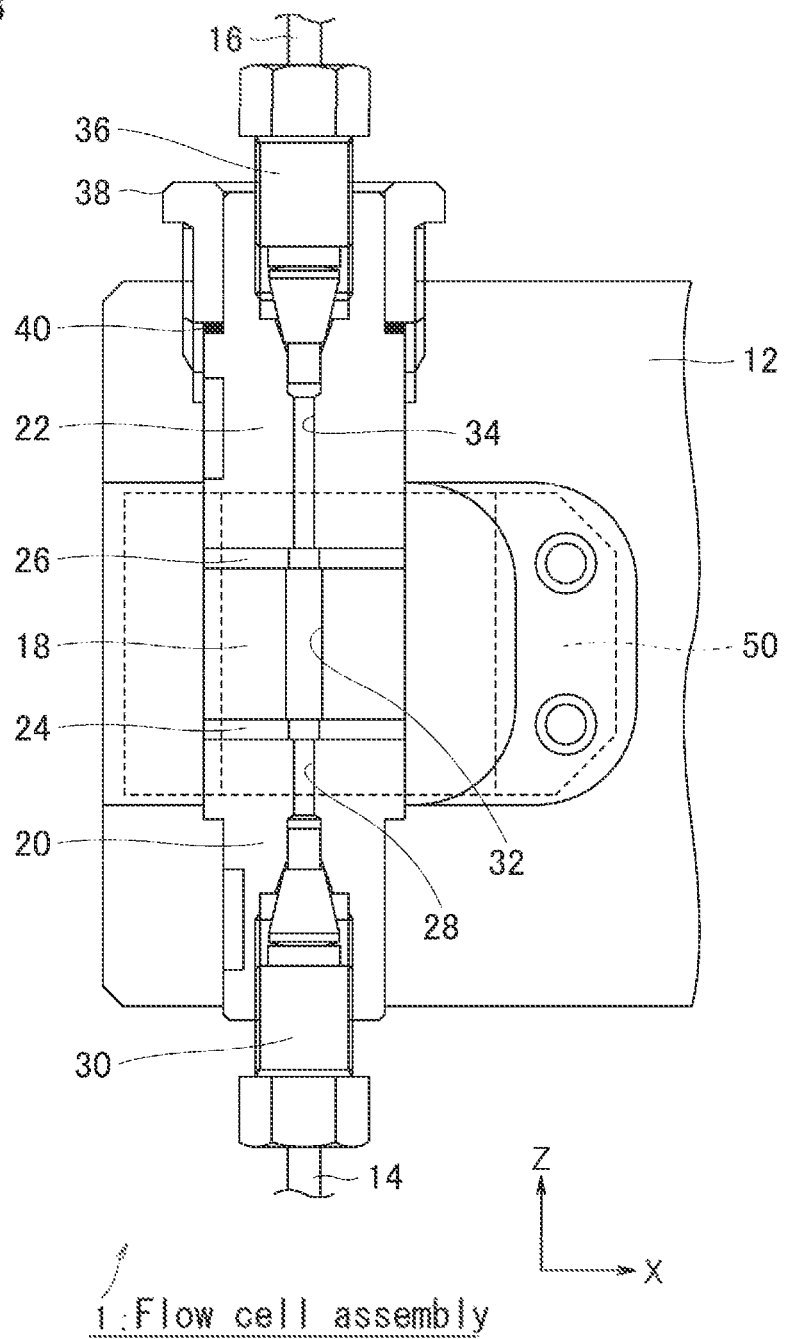

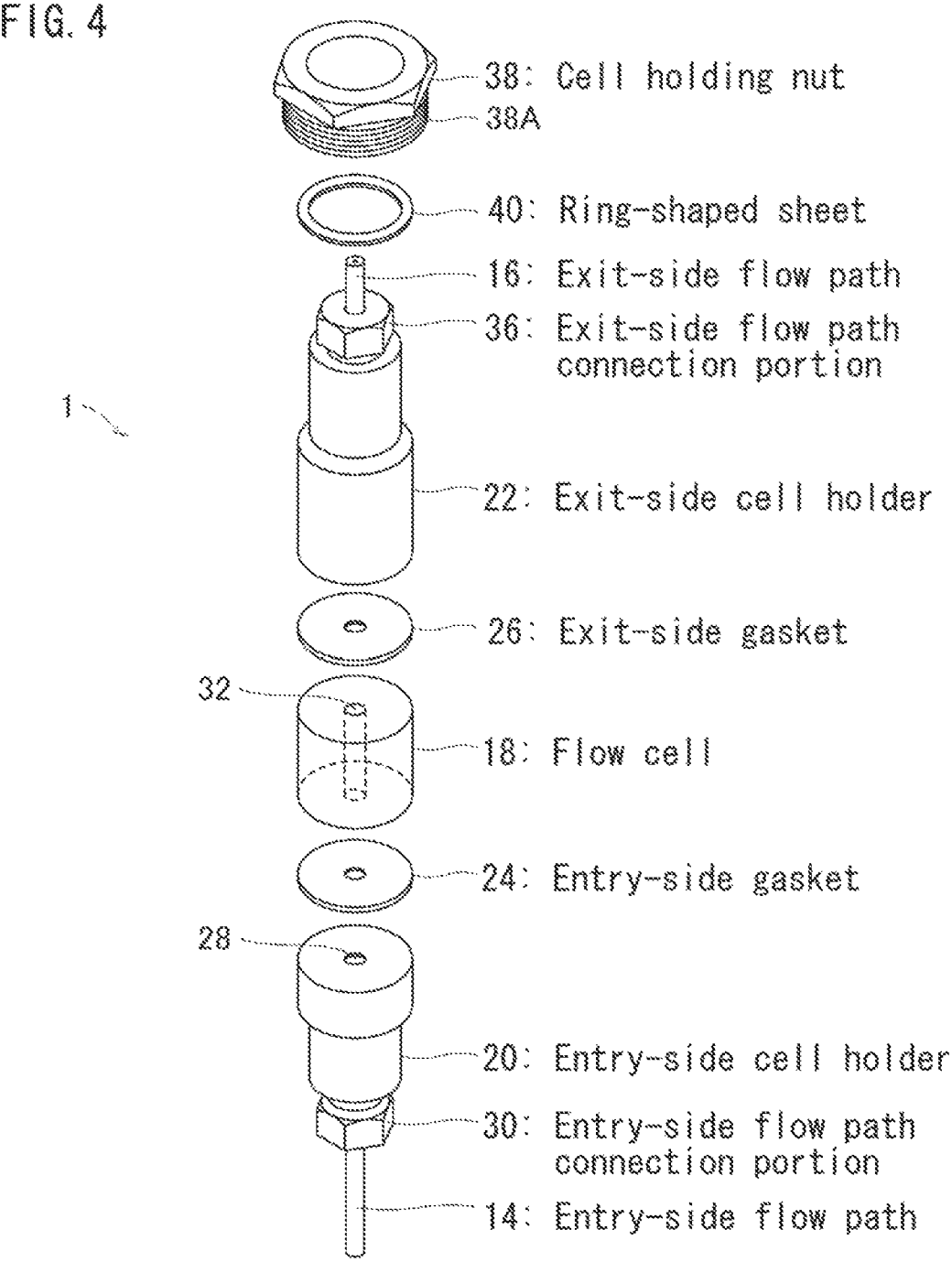

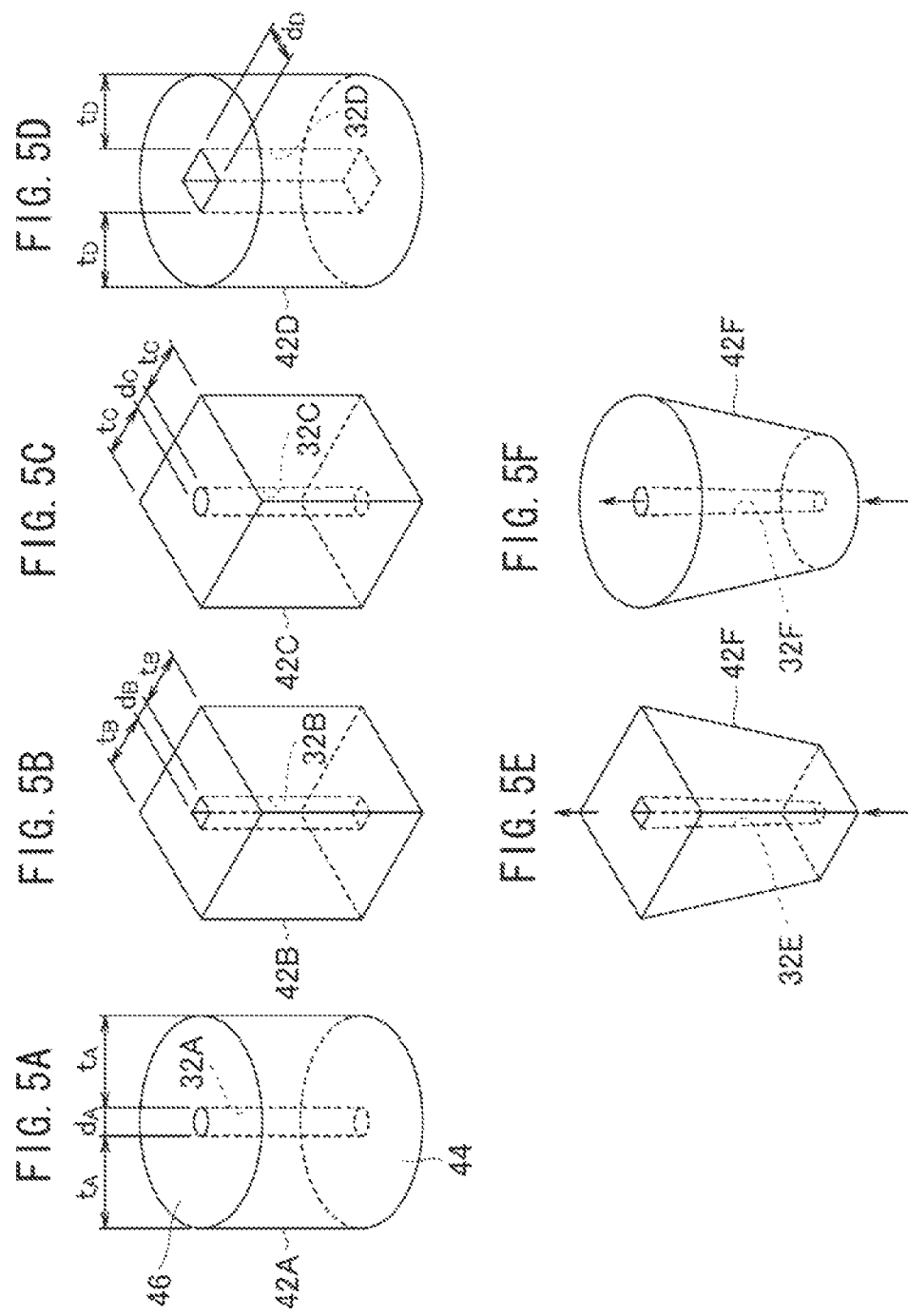

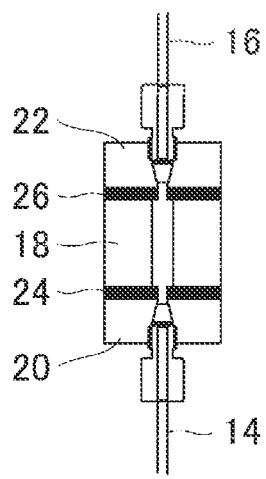
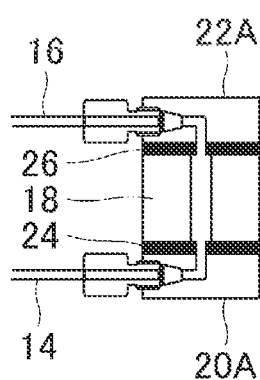
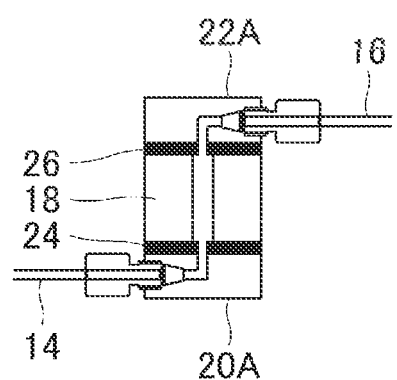
FIG. 6A   FIG. 6B   FIG. 6C
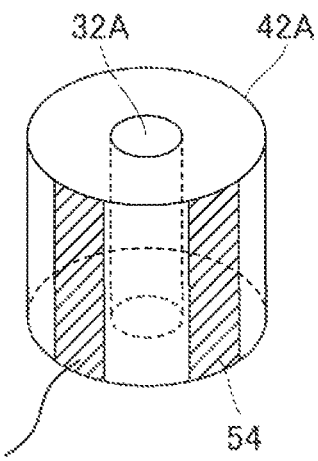
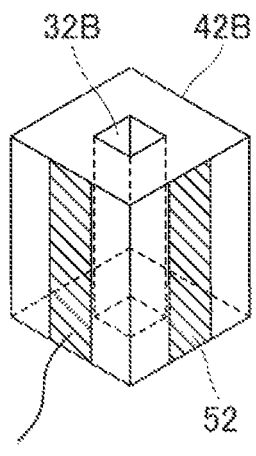
FIG. 7A   FIG. 7B
54: Reflective layer (Reflection means)
52: Reflective layer (Reflection means)

FIG. 9A
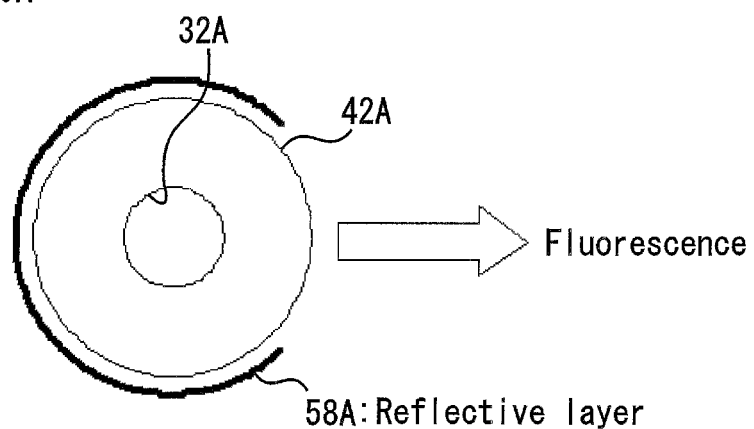
FIG. 9B
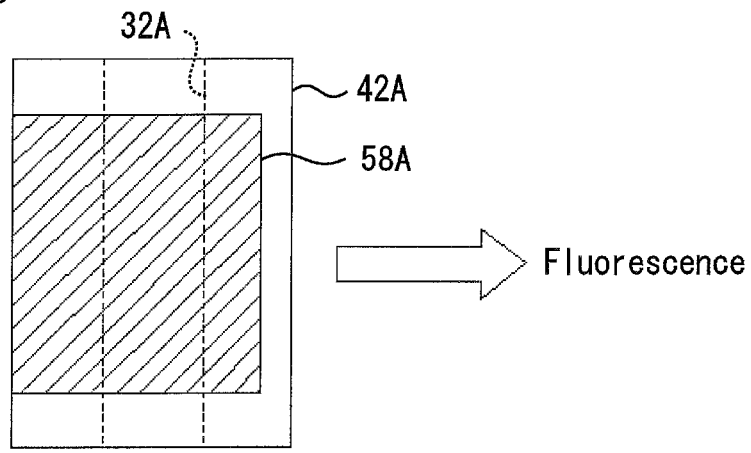
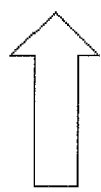
Excitation light

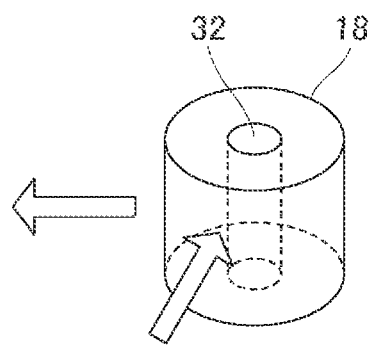
FIG. 10A
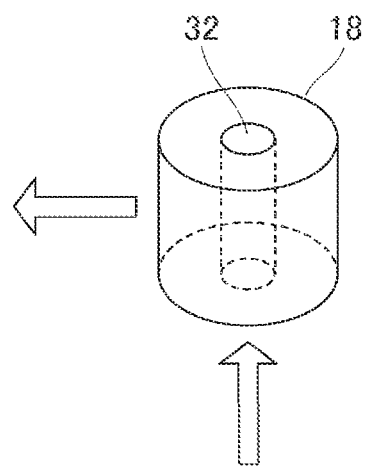
FIG. 10B
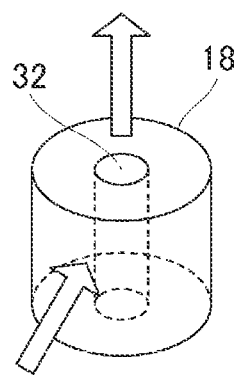
FIG. 10C
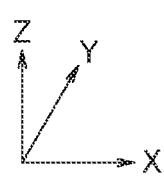

101: Flow cell assembly

118: High-pressure fluorescence flow cell

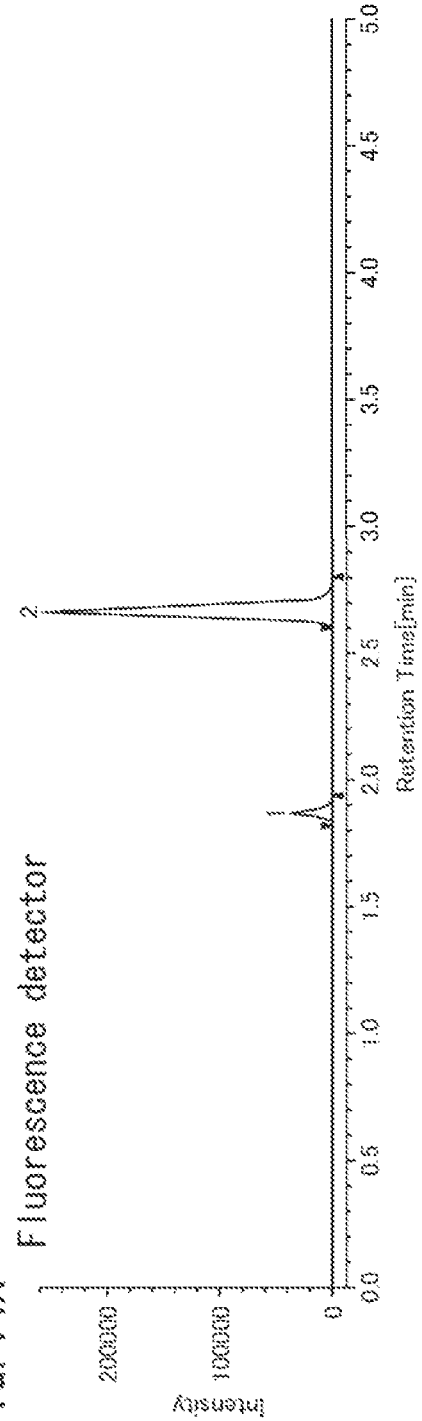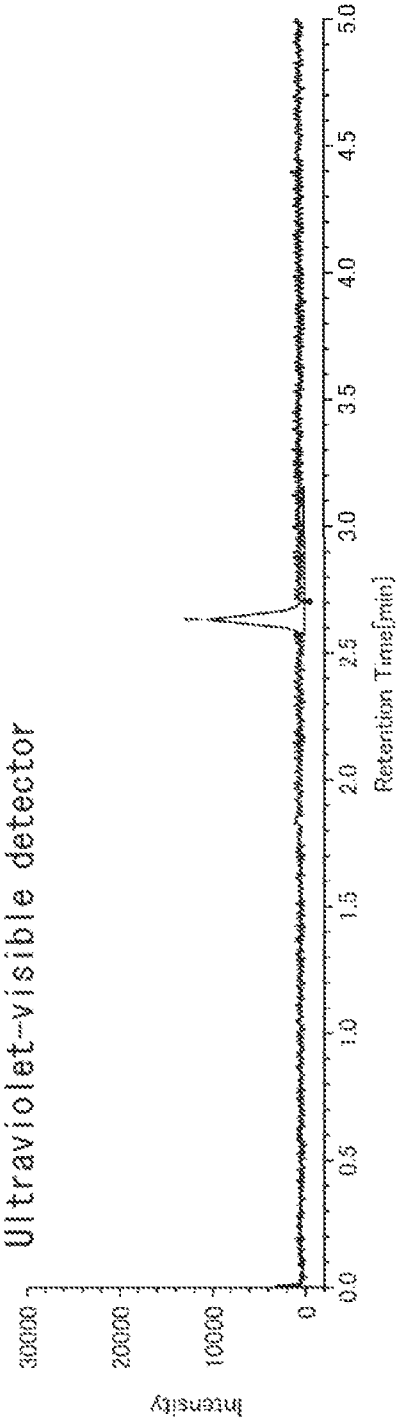

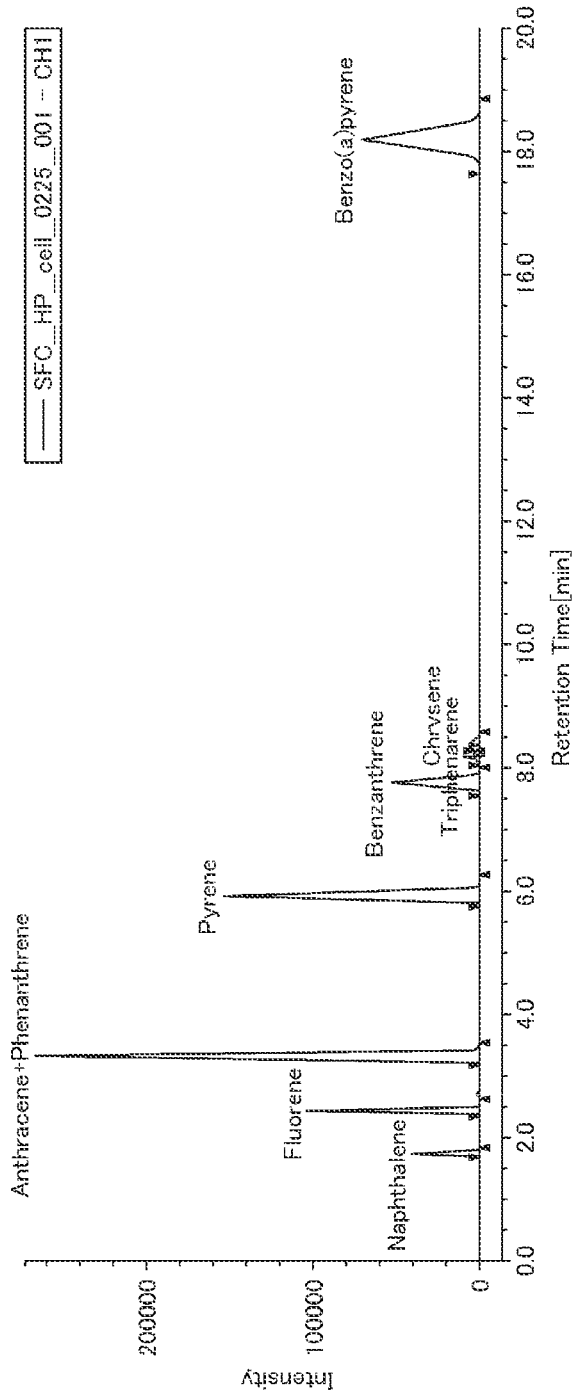

HIGH-PRESSURE FLUORESCENCE FLOW CELL, FLOW CELL ASSEMBLY, FLUORESCENCE DETECTOR, AND SUPERCRITICAL FLUID CHROMATOGRAPH

CROSS-REFERENCE TO RELATED APPLICATIONS

This application is based on and claims the benefits of priority from Japanese Patent Application No. 2011-270374, filed on Dec. 9, 2011, the entire contents of which are incorporated herein by reference.

BACKGROUND OF THE INVENTION

1. Field of the Invention

The present invention relates to high-pressure fluorescence flow cells, assemblies thereof, fluorescence detectors using the high-pressure fluorescence flow cells, and supercritical fluid chromatographs.

2. Description of the Related Art

Supercritical Fluid Chromatograph

Supercritical fluid chromatographs (SFCs) and subcritical fluid chromatographs using carbon dioxide ($CO_2$) as the mobile phase have attracted attention as separation-analysis apparatuses and separation-purification apparatuses that can replace liquid chromatographs (LCs), which utilize an organic solvent. Thanks to the low viscosity and high diffusion coefficient of the fluid utilized as the mobile phase, SFCs can perform quick analysis by increasing the flow velocity without decreasing the column efficiency.

SFCs can be divided broadly into two categories depending on the type of column used. The SFCs utilizing a packed column use techniques developed for liquid chromatographs (LCs), and the SFCs utilizing a capillary column use techniques developed for gas chromatographs (GCs). Since packed-column SFCs developed from LCs are easy to handle and their separation technology is extensible, they have been used to analyze a variety of samples and have been finding a broader range of applications. SFCs are used to separate optical isomers and cc separate polymer oligomers in polymer chain units, are environmentally friendly, and have low running costs. SFCs require a few aftertreatment steps for eliminating the solvent and are suitable for easily-oxidizable material and heat-labile material. In recent studies, SFCs have found wide applications, including separation of achiral matter.

Such separation-analysis apparatuses have also attracted attention from the perspective of environmental conservation. There seems to a tendency to shift from liquid chromatographs (LCs) to supercritical fluid chromatographs (SFCs).

Detectors for Supercritical Fluid Chromatographs

Detectors used for supercritical fluid chromatographs (SFCs) include ultraviolet-visible (UV-VIS) absorbance detectors, evaporative light scattering detectors (ELSDs), and mass spectrometers (MSs). Some of the detectors, such as ultraviolet-visible absorbance detectors, require an optical flow cell. The flow cell for SFCs must have high pressure resistance because the inner pressure reaches 10 MPa or higher.

Fluorescence Detectors

Fluorescence detectors (FLDs) for detecting fluorescence (including phosphorescence) of excited sample constituents also require an optical flow cell, FLDs are used with liquid chromatographs (LCs). The conventional fluorescence detectors have a rectangular flow cell made of silica glass, for example. The sample constituents separated in the column of the LC are introduced successively into the flow cell together with a mobile phase For example, the sample constituents are introduced into the rectangular flow cell from the bottom, travel through an internal flow path, and are drawn out from the top of the flow cell. While they are in the flow path, the sample constituents are irradiated with excitation light from one side of the flow cell. When fluorescence is produced in the sample constituents, the fluorescence is detected in a direction perpendicular to the irradiation direction of the excitation light.

In general separation and analysis of a sample by using a chromatograph, it is important to reduce the volume of the cell to prevent the sample constituents separated in the column from diffusing in the flow cell. For example, low-volume flow cells have been formed by fusing four light-transmissive members made of silica glass into a hollow prismatic shape, as disclosed in Patent Literature 1. By minimizing the cell volume, diffusion of the sample constituents in the cell can be suppressed, and consequently peaks in the detected chromatogram can be sharpened.

In order to prevent the minimized cell volume from lowering the sensitivity of the fluorescence detector, a flow cell configured so allow internal sample constituents to be irradiated efficiently with as much excitation light as possible is used. If the sample is irradiated with excitation light in a direction perpendicular to the flow path of the cell, as the cross section of the flow path in the cell decreases, the optical path length of the cell inevitably decreases. For example, the flow cell disclosed in Patent Literature 2 is configured to direct excitation light parallel to the direction of the flow path. A long optical path length is kept to produce a large amount of fluorescence.

PATENT LITERATURE

Patent Literature 1: Japanese Unexamined Patent Application Publication No. S60-207038

Patent Literature 2: Japanese Unexamined Patent Application Publication No. 2006-300961

In the conventional fused optical flow cells such as those in Patent Literature 1 and Patent. Literature 2, the upper limit of the internal fluid pressure ranges about one to several megapascals (MPa). To use the fluorescence detector in a supercritical fluid chromatograph (SFC), a high-pressure fluorescence flow cell that can withstand a pressure of at least 10 MPa is required. The conventional optical flow cells cannot be used. Therefore, SFCs have not used such a fluorescence detector.

Generally, the fluid is introduced from the column into the flow cell through an inlet tube and is discharged from the flow cell through an outlet tube. To allow fluorescence detection, the cell body is made of a light-transmissive material such as silica glass. If the cell body were made of metal, the inlet, tube could be directly connected to the cell body to form a fluid path. In contrast, the cell body made of a light-transmissive material cannot be connected directly to the connection portion of the inlet tube. As shown in FIG. 7 in Patent Literature 1, the cell body made of silica glass is held vertically between a pair of cell holding members. An inlet hole is formed in the cell holding member on the entry side, and the inlet tube is connected to that cell holding member. An outlet hole is formed in the cell holding member on the exit side, and the outlet tube is connected to that cell holding member. A gasket is placed between the cell body and each of the cell holding members so that the fluid will not leak. To achieve a withstand pressure of 10 MPa or higher in the conventional, flow cells, the cell holding members need to apply a great compressive force to the cell body. However, the conventional fused flow cells could not withstand that force.

SUMMARY OF THE INVENTION

An object of the present invention is to improve the withstanding ability of a flow cell that can be used in a fluorescence (including phosphorescence) detector, giving consideration to the requirement of minimizing the cell volume. Accordingly, is an object of the present invention to provide a fluorescence flow cell which is made of a light-transmissive material, has a withstand pressure of 10 MPa or higher, and can be utilized in fluorescence detection of a high-pressure fluid used in a supercritical fluid chromatograph (SFC) and to provide a fluorescence detector and a supercritical fluid chromatograph that uses the high-pressure fluorescence flow cell.

A high-pressure fluorescence flow cell according to the present invention includes a cell body made of a light-transmissive material, the cell body being penetrated by a straight-line flow path for a high-pressure fluid. The flow path is formed with a cross section of 0.1 mm$^2$ to 5 mm$^2$, both inclusive, orthogonal to its longitudinal direction. The ratio t/d of the wall thickness t (mm) to the width d (mm) of the flow path satisfies formula (1) below $$\frac{t}{d} \geq \frac{1}{2} \times \left[ \sqrt{\frac{\sigma + P}{\sigma - P}} - 1 \right] \times 1.5 \quad (1)$$

where σ indicates the tensile stress (MPa) of the material of the cell, body, and P indicates the withstand pressure (MPa) of the cell body.

It is particularly preferable that the ratio of the wail Thickness to the width of the flow path satisfy t/d≥1.8, which can bring the withstand pressure of the cell body to 40 MPa or higher.

The flow path of the cell, body is formed by boring a block made of the light-transmissive material or by extending a tube made of the light-transmissive material.

If fluorescence in the ultraviolet-visible region is produced in the flow path, the cell body should be made of silica glass or sapphire. If fluorescence in the visible region is produced in the flow path, the cell body should be made of BK7. To detect fluorescence in the ultraviolet-visible region, silica glass is usually used as the light-transmissive material. If a crystalline light-transmissive material such as sapphire is used, a cell body with a higher withstand pressure can be provided.

A flow cell assembly according to the present invention has an inlet hole and an outlet hole of the high-pressure fluid formed before and after the flow path in the high-pressure fluorescence flow cell.

The flow cell assembly includes the high-pressure fluorescence flow cell; an entry-side cell holder that includes the inlet hole for guiding the high-pressure fluid into the flow cell, the inlet hole being disposed to be connected to one opening of the flow path in the flow cell; an exit-side cell holder that includes the outlet hole for outputting the high-pressure fluid from the flow cell, the outlet hole being disposed to be connected to the other opening of the flow path in the flow cell; holding means for holding one of the entry-side cell holder and the exit-side cell holder; and pressing means for pressing the other of the entry-side cell holder and the exit-side cell holder toward the flow cell.

The flow cell is held between the pair of cell holders by a pressing force exerted by the pressing means, and the flow path of the high-pressure fluid is formed from the inlet hole through the flow path in the flow cell to the outlet hole.

Since the pair of cell holders holding the flow cell are disposed at the entry side and the exit side of the flow path, an optical system for irradiating the high-pressure fluid with excitation light in a direction perpendicular to the flow path and detecting fluorescence in a direction perpendicular to both the irradiation direction of the excitation light and the flow path of the high-pressure fluid can be easily configured.

A low-friction sheet is placed between the pressing means and either of the cell holders. The material of the sheet is a fluorine resin or a polyether ether ketone resin (PEEK) or is preferably polychlorotrifluoroethylene resin (PCTFE).

It is preferred in the flow cell assembly according to the present invention that at least one of the inlet hole and the outlet hole be formed in the same straight line as the flow path of the cell body, and an end of the hole be blocked by a window plate made of a light-transmissive material; the cell holder having the window plate have a connecting hole connected to the hole in a part inside the window plate; light be able to enter or exit through the window plate in the longitudinal direction of the flow path; and the high-pressure fluid be able to be input from or output to the outside of the cell holder, through the connecting hole.

With the flow cell assembly, an optical system for irradiating the high-pressure fluid with excitation light through the window plate in the longitudinal direction of the flow cell and detecting fluorescence in the direction perpendicular to the flow path can be adopted. On the contrary, an optical for irradiating the high-pressure fluid with excitation light in the direction perpendicular to the flow path and detecting fluorescence through the window plate in the longitudinal direction of the flow path can be adopted.

A fluorescence detector according to the present invention includes the flow cell assembly, an excitation optical system for delivering excitation light into the cell body of the flow cell assembly, and a light-receiving optical system for receiving fluorescence produced from the high-pressure fluid in the cell body.

A supercritical fluid chromatograph according to the present invention obtains a chromatogram concerning fluorescence by detecting fluorescence of the high-pressure fluid of 10 MPa or higher by using the fluorescence detector.

According to the present invention, a high-pressure fluorescence flow cell with a minimized cell volume and a high withstand pressure can be provided. In other words, a fluorescence flow cell that is made of a light-transmissive material, that has a withstand pressure of 10 MPa or higher, and that can be used to detect fluorescence of a high-pressure fluid in a supercritical fluid chromatograph (SFC) can be provided. A fluorescence detector and a supercritical fluid chromatograph utilizing the high-pressure fluorescence flow cell can be provided.

BRIEF DESCRIPTION OF THE DRAWINGS

FIG. 3 is a longitudinal cross-sectional view of the flow cell assembly.

FIG. 4 is an exploded view of the flow cell assembly.

FIGS. 5A to 5F show modifications of the configuration of a high-pressure fluorescence flow cell according to the present invention.

FIGS. 6A to 6C show modifications of the flow path of a high-pressure fluid in the flow cell assembly.

FIGS. 7A and 7B are views illustrating reflection means in high-pressure fluorescence flow cells according to the present invention.

FIGS. 9A and 9B are views illustrating the incident direction of excitation light to the flow cell with the reflection means and the detection direction of fluorescence from the flow cell.

FIGS. 10A to 10C show modifications of the direction of excitation light entering the high-pressure fluorescence flow cell according to the present invention and the direction of fluorescence detection.

FIGS. 14A and 14B show chromatograms for comparing the results of fluorescence detection by using a supercritical fluid chromatograph of the present invention and ultraviolet-visible detection of anthracene.

FIG. 15 shows a chromatogram obtained as a result of microanalysis of polycyclic aromatic hydrocarbons by using the supercritical fluid chromatograph.

DESCRIPTION OF THE PREFERRED EMBODIMENTS

Fluorescence Detector

Figure 1:
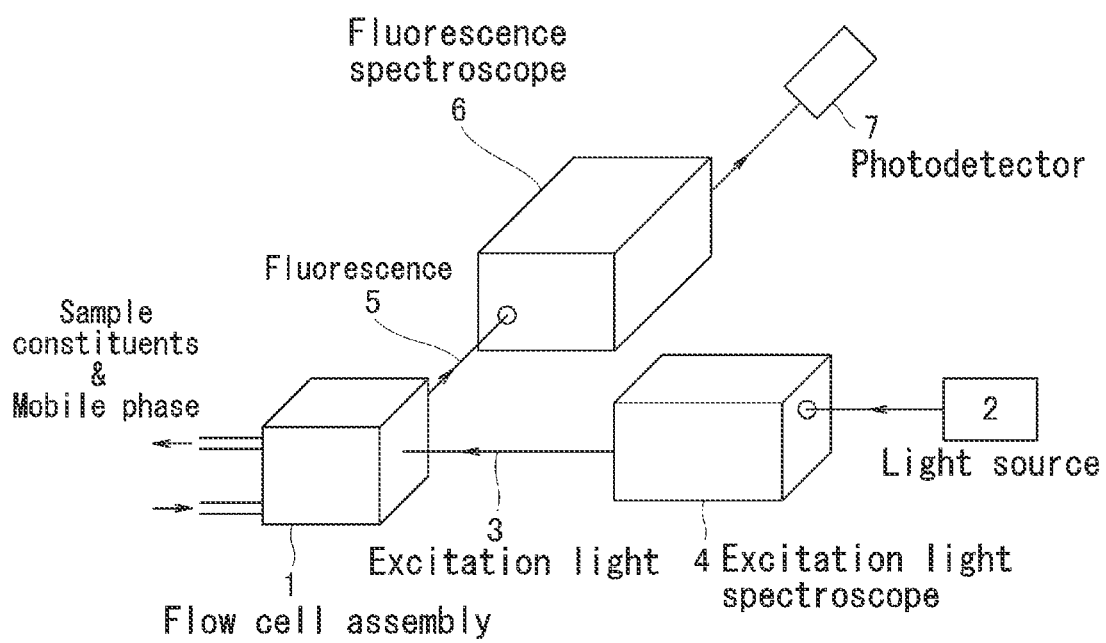
FIG. 1 is a diagram showing the entire configuration of a fluorescence detector according to the present invention.

A fluorescence detector according to the embodiments of the present invention will be described first with reference to FIG. 1. A fluorescence detector 10 shown in the figure includes a flow cell assembly 1, a light source 2, an excitation light spectroscope 4, a fluorescence spectroscope 6, and a photodetector 7.

The fluorescence detector 10 is used as a detector in a supercritical fluid chromatograph (SEC) and detects fluorescence of sample constituents separated in the column. The sample constituents are sent to the flow cell assembly 1 from the column, together with a mobile phase ($CO_2$ or the like). Light emitted from the light source 2, such as a xenon lamp or a mercury lamp, is dispersed by the excitation light spectroscope 4. Dispersed excitation light 3 strikes the sample constituents in the flow cell assembly 1 and produces fluorescence 5 in the sample constituents. The fluorescence 5 exits in a direction orthogonal to the excitation light 3, is dispersed by the fluorescence spectroscope 6, and is then detected by the photodetector 7, such as a photomultiplier. On the basis of the values detected there, a fluorescence chromatogram is obtained. Hereinafter, the excitation light coming from the excitation light spectroscope 4 may be referred to simply as incident light, and the fluorescence of the sample constituents may be referred to simply as output light.

A fluorescence detector according to the present invention is not limited to that having the configuration described above and can be a detector that includes at least an excitation light optical system, a flow cell assembly, and a light receiving system for receiving fluorescence generated in a high-pressure fluid.

First Embodiment

Flow Cell Assembly

Figure 2:
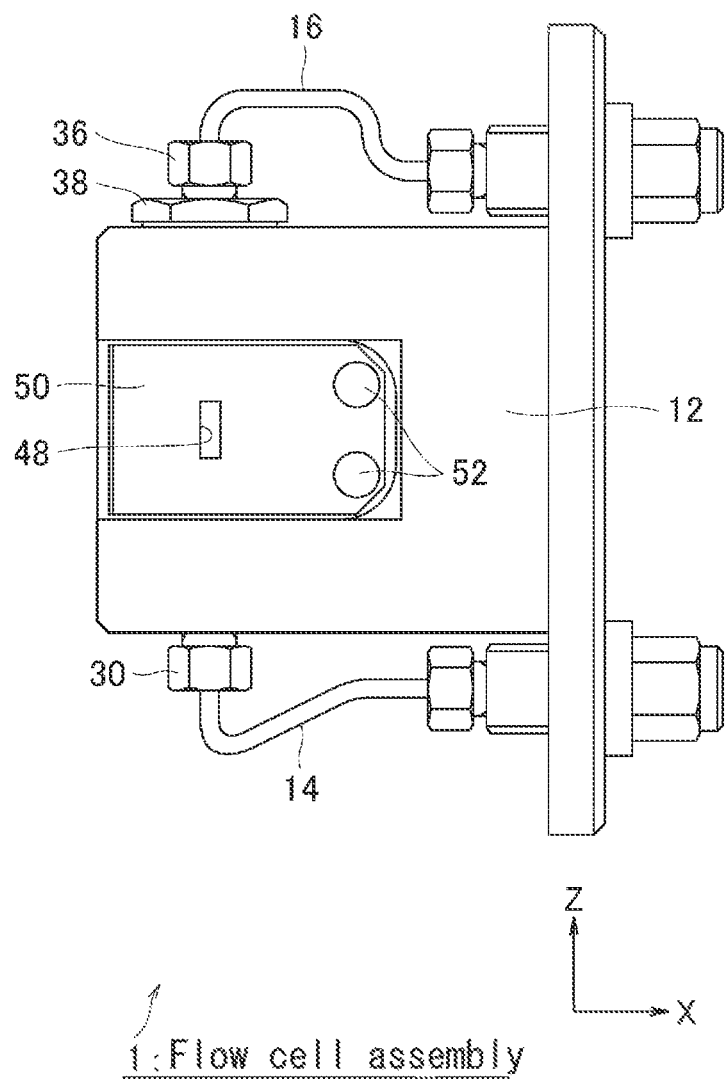
FIG. 2 is an outline drawing of a flow cell assembly according to a first embodiment of the present invention.

The flow cell assembly 1 included in the fluorescence detector 10 will be described next with reference to FIGS. 2, 3, and 4. The flow cell assembly 1 according to a first embodiment shown in FIG. 2 includes a U-shaped holding portion 12 for holding a high-pressure fluorescence flow cell, an entry-side flow path 14 for guiding a high-pressure fluid into the flow cell from the column, and an exit-side flow path 16 for letting the high-pressure fluid flow out of the flow cell.

With reference to a vertical cross-sectional view in FIG. 3 and an exploded view in FIG. 4, the flow cell assembly 1 further includes a flow cell 18, an entry-side cell holder 20 below the flow cell, and an exit-side cell holder 22 above the flow cell. The flow cell 18 is held between the entry-side cell holder 20 and the exit-side cell holder 22 with an entry-side gasket 24 and an exit-side gasket 26 respectively placed therebetween.

Two arm portions (upper and lower arm portions in the figure) separated in the Z direction, of the holding portion 12 are each penetrated with a hole in the Z direction, and the holes share a common central axis. When the entry-side dell holder 20 is inserted into the hole in the lower arm portion, the position of the entry-side cell holder 20 in the Z direction is determined. The entry-side cell holder 20 has an inlet hole 28 formed in the Z direction at the center thereof. The entry-side flow path 14 is connected to the entry-side cell holder 20 by an entry-side flow path connection portion 30 and is connected to the inlet hole 28

The cylindrical flow cell 18 is placed on top of the entry-side cell holder 20 with the entry-side gasket 24 placed between them. An intra-cell flow path 32 penetrates the center of the flow cell 18 in the Z direction and is connected in a straight line to the inlet hole 28 in the entry-side cell holder 20.

The exit-side cell holder 22 inserted into the hole in the upper arm portion of the holding portion 12 is placed on top of the cylindrical flow cell 18 with the exit-side gasket 26 placed between them. The exit-side cell holder 22 has an outlet hole 34 formed in the Z direction at the center thereof, and the outlet hole 34 is connected to the flow path 32 in the flow cell 18. The exit-side flow path 16 is connected to the top of the exit-side cell holder 22 with an exit-side flow-path connection portion 36 and is connected to the outlet hole 34. In the upper arm portion, an internal thread is formed on the inner surface of the hole into which the exit-side cell holder 22 is inserted. An external thread 38A. (see FIG. 4) to be engaged with the internal, thread is formed on the outer surface of a cell holding nut 38 provided as pressing means.

When the cell holding nut 38 is screwed in, the exit-side cell holder 22 is pressed toward the flow cell 18. The compressive force exerted on the flow cell 18 in the Z direction deforms the gaskets 24 and 26, creating a tight seal between the flow cell 18 and the upper cell holder 22 and between the flow cell 18 and the lower cell holder 20. Consequently, a straight-line path with a withstand pressure of 10 MPa or higher is formed from the entry-side flow path 14 through the inlet hole 28, the intra-cell flow path 32, and the outlet hole 34 to the exit-side flow path 16.

High-pressure Florescence Flow Cell

The high-pressure fluorescence flow cell (hereinafter referred to simply as the flow cell 18) used in this embodiment has a cylindrical cell body 42A made of a light-transmissive material such as silica glass (amorphous structure), as shown in FIG. 5A. The cell body 42A has a straight-line intra-cell flow path (through-hole) 32A. The cell body 42A is formed by boring the round-columnar intra-cell flow path 32A in a round-columnar silica-glass block. The entry-side opening and the exit-side opening of the intra-cell flow path 32A are respectively formed in the bottom face and top face (an entry-side face 44 and an exit-side face 46) of the cylindrical body. The entry-side face 44 and the exit-side face 46 are parallel to each other.

FIGS. 5B to 5F show modifications of the cell body 42A. A cell body 42B shown in FIG. 5B is formed by boring a prismatic intra-cell flow path 32B in a prismatic silica-glass block. A cell body 42C shown in FIG. 5C is formed by boring a round-columnar intra-cell flow path 32C in a prismatic silica-glass block. A cell body 42D shown in FIG. 5D is formed by boring a prismatic intra-cell flow path 32D in a round-columnar silica-glass block.

A cell body 42E shown in FIG. 5E is formed by boring a prismoidal intra-cell flow path 32E in a prismoidal block. The cross section of the intra-cell flow path 32E may be enlarged from the entry side to the exit side at a constant rate. A cell body 42F shown in FIG. 5F is formed by boring a truncated conical intra-cell flow path 32F in a truncated conical silica-glass block. If the outer wall of the cell body and the inner wall of the intra-cell flow path are not parallel to the central axis of the flow path, as in the cell body 42E having the prismoidal intra-cell flow path 32E and the cell body 42F having the truncated conical intra-cell flow path 32F, retention of the sample constituents in the intra-cell flow path can be suppressed efficiently. If excitation light strikes the cell body perpendicularly to the central axis of the intra-cell flow path, the excitation light does not strike the outer wall of the cell body or the inner wall of the intra-cell flow path perpendicularly and is reflected in a direction other than the direction perpendicular to the center axis of the intra-cell flow path. Since fluorescence is normally detected in the direction perpendicular to the central axis of the intra-cell flow path, the light reflected in a direction other than the direction perpendicular to the center axis of the intra-cell flow path will not travel toward the fluorescence detector, lowering the background signal level of the fluorescence detector. Consequently, fluorescence can be detected with less noise.

In the cell body 42A shown in FIG. 5A, the ratio $t_A/d_A$ of the wall thickness $t_A$ to the diameter $d_A$ of the round-columnar intra-cell flow path 32A satisfies formula (1) given below. In the cell body 42B shown in FIG. 5B, the ratio $t_B/d_B$ of the wall thickness $t_B$ to the width $d_B$ of the prismatic intra-cell flow path 32B also satisfies formula (1). In the cell body 42C shown in FIG. 5C, the ratio $t_C/d_C$ of the wall thickness $t_C$ to the diameter $d_C$ of the round-columnar intra-cell flow path 32C also satisfies formula (1). In the cell body 42D shown in FIG. 5D, the ratio $t_D/d_D$ of the wall thickness $t_D$ to the width do of the prismatic intra-cell flow path 32D also satisfies formula (1). In the cell body 42E shown in FIG. 5E and the cell body 42F shown in FIG. 5F, the ratio of the wall thickness to the width of the intra-cell flow path also satisfies formula (1).

The material of the cell bodies 42A to 42F in FIGS. 5A to 5F is silica glass or sapphire if fluorescence in the ultraviolet-visible region is produced in the intra-cell flow path. If fluorescence in the visible region is produced, the material is a general optical glass such as BK7.

The cell bodies 42A to 42F achieve the required withstand pressure by increasing the wall thickness of the intra-cell flow path sufficiently. The general relationship between the wall thickness and the withstand pressure of the glass tube is expressed as follows.

$$P = \frac{1 - \left(\frac{d}{D}\right)^2}{1 + \left(\frac{d}{D}\right)^2} \times \sigma \quad (2)$$

Here, P is the permissible internal pressure or withstand pressure (MPa), σ is the tensile stress (MPa), which is 47 MPa with silica glass and 2250 MPa with sapphire, d is the inside diameter (mm) of the light-transmissive material, and D is the outside diameter (mm) of the light-transmissive material.

As indicated above, a cell body made of sapphire has a higher withstand pressure P than one made of silica glass. However, silica glass has higher optical transmissive characteristics than sapphire. Silica glass is usually used in fluorescence detection in the ultraviolet-visible region, and sapphire is used when a higher withstand pressure is required.

The outside diameter D of the cell body can be obtained from the inside diameter d and the wall thickness t of the intra-cell flow path: D=d+2t. From formula (2), a formula expressing the ratio of the wall thickness to the inside diameter (t/d) is derived as follows.

$$\frac{t}{d} = \frac{1}{2} \times \left[\sqrt{\frac{\sigma + P}{\sigma - P}} - 1\right] \quad (3)$$

The table below shows the relationship between the withstand pressure P and t/d satisfying formula (3), for silica glass and sapphire.

| WITHSTAND PRESSURE P (MPa) | (SILICA GLASS) t/d | (SAPPHIRE) t/d |
|---|---|---|
| 10 | 0.120593 | 0.002227 |
| 15 | 0.195971 | 0.003345 |
| 20 | 0.287636 | 0.004464 |
| 25 | 0.404534 | 0.005587 |
| 30 | 0.564121 | 0.006712 |
| 35 | 0.807032 | 0.007839 |
| 40 | 1.262709 | 0.008969 |

The cross section of the intra-cell flow path suitable for practical use ranges from 0.1 mm² to 5 mm², both inclusive. The table below shows the relationship between the inside diameter d and the cross section of an intra-cell flow path having a circular cross section.

| INSIDE DIAMETER d(mm) OF INTRA-CELL FLOW PATH | CROSS SECTION (mm²) OF INTRA-CELL FLOW PATH |
|---|---|
| 0.1 | 0.007854 |
| 0.3 | 0.070686 |
| 0.6 | 0.282743 |
| 1.0 | 0.785398 |
| 1.5 | 1.767146 |
| 2.0 | 3.141593 |
| 2.5 | 4.908739 |
| 5.0 | 19.63495 |

As indicated by formula (3) above, the ratio t/d of the wall thickness to the inside diameter depends on the material (tensile strength σ) of the cell body and the required withstand pressure P.

Since the practical withstand pressure in supercritical fluid chromatographs (SFCs) and subcritical fluid chromatographs is about 10 to 40 MPa, the withstand pressure P could be set to about 40 MPa.

Since silica glass has higher ultraviolet transmission, silica glass is preferred. If it is difficult to achieve the required withstand pressure with silica glass, sapphire is used.

The inventors have found that a flow cell having a required withstand pressure (MPa) can be provided by forming a cell body in which the ratio t/d of the wall thickness t (mm) to the width d (mm) of the intra-cell flow path satisfies formula (1), irrespective of the material of the cell body and the shape of the cross section of the cell body or the intra-cell flow path.

$$\frac{t}{d} \geq \frac{1}{2} \times \left[ \sqrt{\frac{\sigma + P}{\sigma - P}} - 1 \right] \times 1.5 \quad (1)$$

Here, σ is the tensile stress (MPa) of the material of the cell body.

To obtain a cell body made of silica glass (tensile stress of 47 MPa) with a withstand pressure P of 40 MPa, t/d must be 1.2 or higher, according to formula (3). In the actual design, however, the safety factor α is generally set to 1.5 or higher, preferably set to 2.0 or higher. When the safety factor α is 1.5, t/d is 1.8 or higher. When the safety factor α is 2.0, t/d is 2.4 or higher. In short, it has been found that the cell body should be designed with t/d≥1.8, preferably designed with t/d≥2.4, and that a t/d value satisfying formula (1) should be used.

Although the design value of t/d≥1.8 or t/d≥2.4, is obtained from silica glass, the same design value can be applied to sapphire. The wall thickness t calculated from the strength (tensile stress of 2250 MPa) of sapphire based on formula (1) is very small, but the actual wall thickness becomes greater because of limitations on machining and the relationship with a fluid seal. The value calculated with the formula (3) indicates the relationship between the withstand pressure P and the wall thickness t of the pipe material, irrespective of whether the material is silica glass or sapphire. Since the actual flow cell may receive additional force, the actual wall thickness t should be greater than the value obtained from formula (3). Giving consideration to those points, the inventors have found that, by using a t/d value satisfying formula (1), the object of the present invention can be achieved and that t/d≥1.8, preferably t/d≥2.4 can be applied to any material.

The flow cell assembly 1 in this embodiment has a slit 48 (see FIG. 2) on the incident side of the flow cell 18 to reduce stray light. The slit 48 is an elongated rectangular hole formed in a slit plate 50, and the slit plate 50 is secured to the holding portion 12 by setscrews 52. To prevent the retention of the sample constituents in the intra-cell flow path 32 of the flow cell 18, the width of the intra-cell flow path 32 should be minimized. To shine excitation light efficiently into the intra-cell flow path 32, the slit 48 and the intra-cell flow path 32 should have an equal width.

If the slit 48 and the intra-cell flow path 32 have an extremely small width, the amount of fluorescence will be reduced, and the sensitivity will be lowered. Therefore, the slit 48 on the incident side and the intra-cell flow path 32 should have a suitably small width around 0.5 to 2.0 mm. It used to be very difficult to bore a round-columnar or truncated conical intra-cell flow path 32 having such a small width in a silica-glass block. Technology for extension machining of glass or quartz developed for grinding processes and optical fiber fabrication (wiredrawing) processes has been improved, and a narrow flow path having a width of about 0.5 to 2.0 mm can now be formed with a desired precision.

The sample dimensions of the cell body 42A shown in FIG. 5A are as follows:

Diameter of cell body: 10.0 mm
Diameter of intra-cell flow path: 1.8 mm
Length of intra-cell flow path: 7.5 mm The intra-cell flow path 32A with these dimensions will allow a sufficient amount of excitation light to enter. The diameter of the cell body is calculated to provide a withstand pressure of about MPa on the basis of formula (1). The sample wall thickness t of the intra-cell flow path is 4.1 mm, about 2.3 times the diameter d (1.8 mm) of the intra-cell flow path.

In this embodiment, the cell bodies 42A to 42F are formed by boring the intra-cell flow path in a silica-glass block. The cell body may also be formed by extending a tube made of silica glass.

The path of a high-pressure fluid flowing through the flow cell assembly 1 will be described with reference to FIGS. 6A to 6C. The paths shown in the figures have the same flow path in the flow cell 18 but different paths in the inlet hole in the entry-side cell holder 20 and the outlet hole in the exit-side cell holder 22. FIG. 6A is a simplified view of the flow cell assembly 1 shown in FIG. 3. The entry-side flow path and the exit-side flow path adjacent to the flow cell 18 form a straight-line path together with the intra-cell flow path. This assembly shows the smallest influence of retention in the flow path.

The entry-side flow path 14 and the exit-side flow path 16 may be connected respectively to an entry-side cell holder 20A and an exit-side cell holder 22A perpendicularly with respect to the intra-cell flow path in the flow cell 18, as in the flow cell assemblies shown in FIGS. 6B and 6C, depending on the traveling directions of incident light and output light. FIG. 6B shows a U-shaped path of high-pressure fluid, and FIG. 6C shows a Z-shaped path of high-pressure fluid. Flow assemblies having different paths can be configured by using the same cell body 18.

In the flow cell assembly, two cell holders compress the flow cell 18 to prevent the high-pressure fluid from leaking through a gap between the flow cell 18 and the entry-side or exit-side cell holder, that is, to provide the flow cell assembly with sufficient withstand pressure. The pressurization method of the flow cell 18 was described with reference to FIGS. 3 and 4. In the flow cell assemblies shown in FIGS. 6A, 6B, and 6C, when the cell holding nuts are tightened, a large compressive force is exerted on the flow cell 18. In this embodiment, the gaskets 24 and 26 made of polytetrafluoroethylene (PTFE) or polyether ether ketone resin (PEEK) are placed between the flow cell 18 and the cell holder 20 or 20A and between the flow cell 18 and the cell holder 22 or 22A so that the flow cell 18 made of a light-transmissive material will not be damaged by pressurization. For example, in a flow cell assembly using the tubular cell body 42A shown in FIG. 5A, a tightening torque for the cell holding nut, calculated to provide a withstand pressure of 40 MPa, is 2.5 N·m. As the gaskets 24 and 26, toroidal packing having a thickness of 0.3 mm (outside diameter of 9.9 mm and inside diameter of 2.5 mm) can be used, for example.

In this embodiment, a ring-shaped sheet 40 made of polychlorotrifluoroethylene (PCTFE) or the like is placed between the exit-side cell holder 22 and the cell holding nut 38, as shown in FIGS. 3 and 4. Since the PCTFE sheet has low friction, when the cell holding nut 38 is tightened, the exit-side cell holder 22 will not turn to damage or move the flow cell 18.

By using the ring-shaped sheet 40, the flow cell 18 can be pressurized evenly. Slackness in the ring-shaped sheet 40 can be removed by tightening the cell holding nuts 38 at a predetermined torque about three times at intervals of about 10 minutes. Then, the flow cell 18 can be pressurized more evenly. Through even pressurization, the flow cell 18 can be protected from damage resulting from partial stress and from a drop of withstand pressure with the lapse of time.

The ring-shaped sheet 40 used as a slip material may be made of a fluorine resin or polyether ether ketone resin (PEEK), as well as PCTFE.

As shown in FIGS. 7A and 7B, reflective layers (or reflective plates) 54 or 52 may be provided on the side face of the cell body 42A or 42B to improve the detection sensitivity. Two hatched areas in the figures are opposite to the area irradiated with excitation light with respect to the intra-cell flow path 32A or 32B and opposite to the fluorescence output area with respect to the intra-cell flow path 32A or 32B. When the reflective layers are provided to face the irradiated area and the output area of the cell body 42A or 42B, the amount of light can be increased with the light reflected at the reflective layers, consequently improving the detection sensitivity. The reflective layers 54 or 52 may be formed by vapor-depositing aluminum on the outer wall of the cell body 42A or 42B, by attaching flat mirrors firmly to the outer wall of the cell body 42A or 42B, or by placing concave mirrors at a short distance from the outer wall.

When collective lenses, not shown in the figures, are placed in the directions of the light entering and exiting the cell body 42A or 42B, the loss of light can be reduced.

Figure 8A:
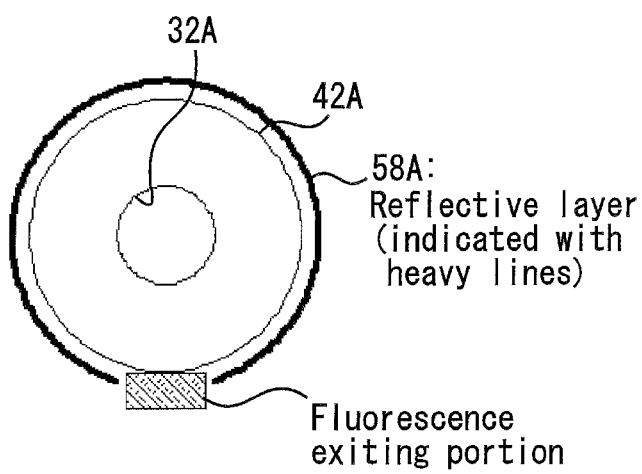
FIGS. 8A to 8D are views illustrating other reflection means in high-pressure fluorescence flow cells according to the present invention.
Figure 8C:
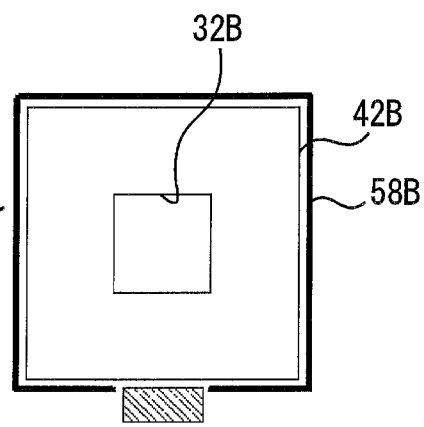
Figure 8B:
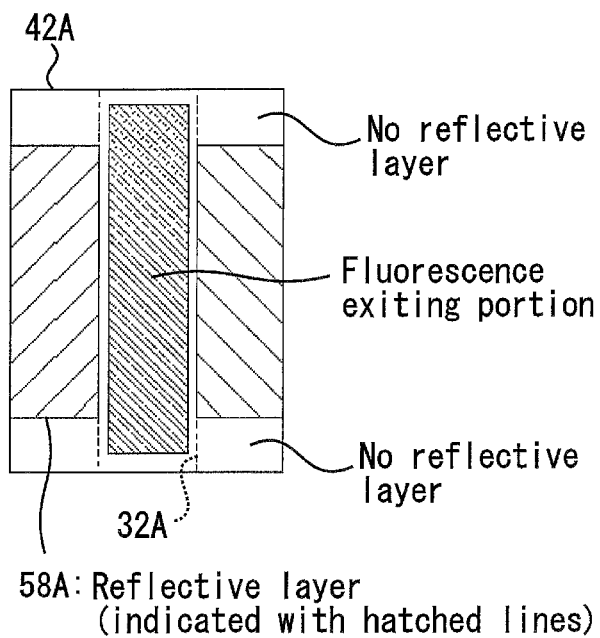
Figure 8D:
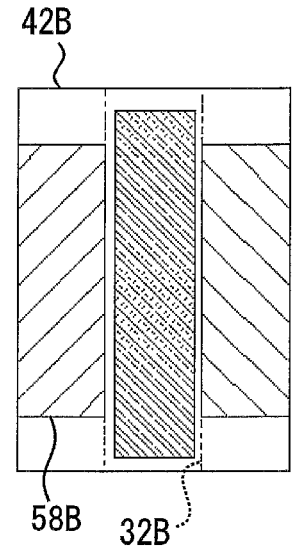

The area of the flow cell that be covered with the reflective layer is not restricted to the area shown in FIG. 7A, 7B. That area may be set as shown in Fig. 8A to 8D. The cell body 42A, 42B shown in FIG. 8A, 8C has a reflective layer 58A, 58B so as to cover almost the whole of the side peripheral surface of the cell body 42A, 42B. An area that is not covered with the reflective layer is formed as a slit as shown in FIG. 8B, 8D. Since fluorescence goes out of the cell through this slit, this slit is called a window for fluorescence.

The sample constituents irradiated with excitation light that is delivered along to the central axis of the flow path generate fluorescence. The fluorescence is emitted in all directions in the cell irrespective of the incident direction. A part of the fluorescence passes directly to the window for fluorescence. Another part of the fluorescence passes to the window for fluorescence after having reflected the reflective layer. Consequently, the flow cell with the reflective layer shown in FIG. 8A to 8D can more effectively lead the fluorescence into the fluorescence spectroscope compared with the flow cell shown in FIG. 7A, 7B. In particular, the flow cell can effectively lead the fluorescence into the fluorescence spectroscope under the condition that the shape of the reflective layer is cylindrical, elliptic cylindrical, or tubular with parabolic cross-section. The cylindrical shape has the central axis of the flow path at the center. The elliptic cylindrical shape has the central axis of the flow path at one focus of the ellipse. And, the elliptic cylindrical shape has the inlet port of the fluorescence spectroscope at another focus of the ellipse. The tubular shape having parabolic cross-section has the central axis of the flow path at the focus of the parabola.

FIGS. 9A and 9B are views illustrating the incident direction of excitation light to the flow cell and the detection direction of fluorescence from the flow cell. Thus, the reflective layer 58A, 58B are suitable for the flow cell that has the optical configuration which excitation light enters parallel to the central axis of the flow path 32A, 32B, and fluorescence exits perpendicularly to the central axis of the flow path 32A, 32B.

Moreover, the reflective layer should not cover close to the both edge of the flow cell body in the direction of the flow path. If the reflective layer covers an area close to the edge of the cell body in the direction of the flow path, scattered light of the excitation light by the cell holder generally made of metal or/and gasket generally made resin is led in larger quantities to the fluorescence spectroscope. Consequently, a background level rises and interferes with the high sensitivity measurement. Thus, more preferably, in order to reduce a large amount of the scattered light in exchange for reduction of a small amount of the fluorescence, the area close to the edge in the direction of the flow path may not be covered with the reflective layer.

Instead of the reflective layers 58A or 58B, the reflection member which can realize a similar function may be arranged around the cell body 42A, 42B.

Second Embodiment

In fluorescence measurement by using the flow cell assembly 1 according to the first embodiment, excitation light is delivered perpendicularly (Y direction) to the central axis of the intra-cell flow path 32, and fluorescence exits perpendicularly (X direction) to the central axis of the intra-cell flow path 32, as shown in FIG. 10A. The incident direction (Y direction) and the output direction (X direction) are in a plane perpendicular to the intra-cell flow path 32 and are at right angles to each other. In FIG. 10A, since the incident light and output light are at right angles to each other with respect to the flow cell 18, it becomes difficult for the incident light to get into the output light, thus improving the sensitivity.

The flow cell 18 can also be used in different ways as shown in FIGS. 10B and 10C. In FIG. 10B, excitation light enters parallel to the central axis of the intra-cell flow path 32, and fluorescence exits perpendicularly to the central axis of the intra-cell flow path 32. In FIG. 10C, excitation light enters perpendicularly to the central axis of the intra-cell flow path 32, and fluorescence exits parallel to the central axis of the intra-cell flow path 32. The three uses illustrated in FIGS. 10A to 10C can be applied to each type of the flow cells shown in FIGS. 5A to 5F.

Figure 11:
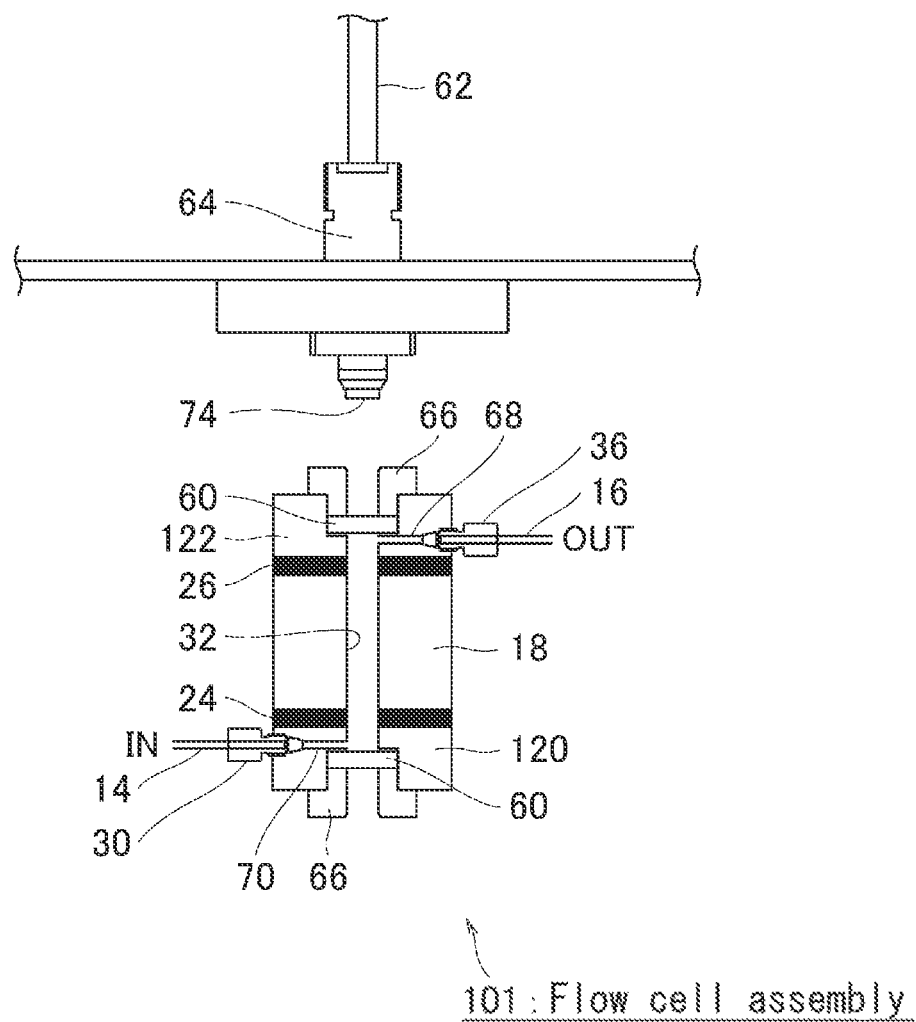
FIG. 11 is an outline drawing of a flow cell assembly according to a second embodiment of the present invention.

A flow cell assembly 101 according to a second embodiment, which enables the use illustrated in FIG. 10B, will be described below in detail. The flow cell assembly 101 is configured as shown in FIG. 11. The figure shows a flow cell 18, gaskets 24 and 26, an entry-side cell holder 120, an exit-side cell holder 122, and a route through which excitation light is guided, and omits the other components.

In this embodiment, both the entry-side cell holder 120 and the exit-side cell holder 22, or either one of the two cell holders has a window plate 60 which transmits excitation light. The guiding route of the excitation light is formed by an optical fiber 62 and a fiber connection portion 64. Excitation light is guided into the intra-cell flow path 32 by the optical fiber 62 through the window plate 60 in the exit-side cell holder 122.

An outlet hole of the exit-side cell holder 122 is formed in the same straight line as the intra-cell flow path 32 of the flow cell 18, and an end of the outlet hole is blocked by the window plate 60 made of a light-transmissive material. The window plate 60 is secured to the exit-side cell holder 122 by a window-plate holder 66. The exit-side cell holder 122 also has an exit-side connecting hole 68 connected to the outlet hole in a direction perpendicular to the longitudinal direction of the intra-cell flow path 32, in an inner part of the window plate 60.

The high-pressure fluid is discharged through the intra-cell flow path 32, the outlet hole, and the exit-side connecting hole 68 to the exit-side flow path 16.

In the flow cell assembly 101, excitation light can enter through the window plate 60 in the longitudinal direction of the intra-cell flow path 32, and the high-pressure fluid is discharged through the exit-side connecting hole 68 in the exit-side cell holder 122. In this embodiment, the entry-side cell holder 120 also has the window plate 60, the window-plate holder 66, and an entry-side connecting hole 70, and these components are configured in the same manner as in the exit-side cell holder 122. Excitation light enters the outlet hole through the window plate 60 of the exit-side cell holder 122 and produces fluorescence in the sample constituents in the straight-line path formed by the outlet hole, the intra-cell flow path 32, and the inlet hole. The excitation light reaches the inlet hole of the entry-side cell holder 120, travels straight ahead, and exits from the entry-side window plate 60. Fluorescence produced by the sample constituents is emitted in all directions, and a part of the fluorescence getting in the direction of fluorescence detection is guided to the fluorescence spectroscope. The direction of fluorescence detection is perpendicular to the central axis of the intra-cell flow path 32.

In the example shown in FIG. 11, the direction in which the excitation light travels (from top to bottom in the figure) is opposite to the direction in which the fluid flows (from bottom to top in the figure). The two directions may be the same. The difference in directions will not produce a substantial difference.

The entry-side cell holder can be the same as the entry-side cell holder in the first embodiment and is not necessarily provided with the window plate 60, unlike in this embodiment.

The excitation light is guided by the optical fiber 62 to the vicinity of the window plate 60 in the exit-side cell holder 122. More specifically, by placing an irradiation aperture 74 of the fiber connection portion 64 toward the window plate 60 of the assembly 1 near the window plate 60, as shown in FIG. 11, the excitation light can be guided through the window plate 60 into the intra-cell flow path 32 of the flow cell 18. With the use of the optical fiber 62, the excitation light can be directed efficiently only into the intra-cell flow path 32 having a small cross section, and scattering of the excitation light and stray light caused by reflection can be reduced. Therefore, the detection sensitivity can be improved. The optical fiber 62 is suitable for guiding incident light onto a very small surface such as the window plate 60 in this embodiment and can produce the effects described above.

In this embodiment, the excitation light 3 emitted from the excitation light spectroscope 4 may be guided to the window plate 60 by light guiding means based on a usual optical system, instead of the means for guiding excitation light using an optical fiber.

Figure 12A:
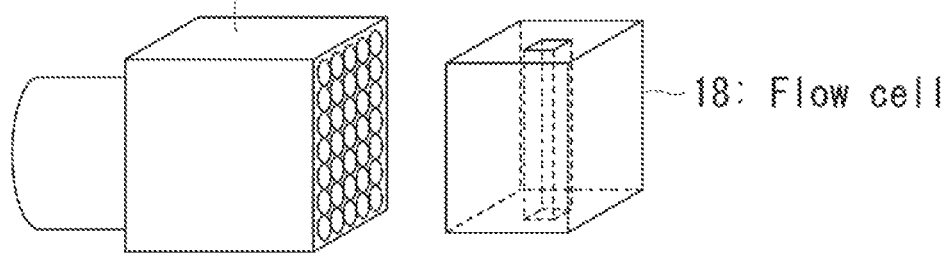
FIGS. 12A and 12B are views illustrating the positional relationships between fiber bundles and the flow cell according so the present invention.
Figure 12B:
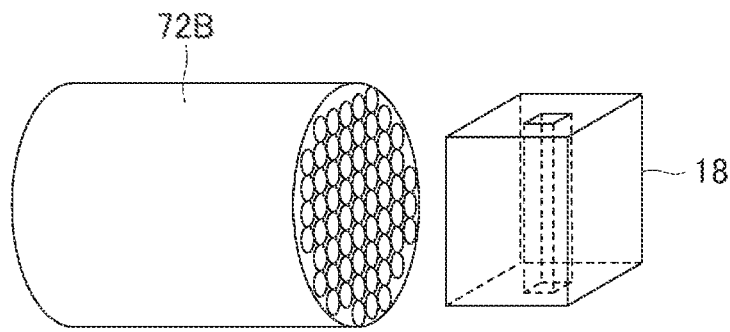

Light collecting means for collecting fluorescence from the flow cell 18 and guiding the collected light to the fluorescence spectroscope in the first and second embodiments will be described with reference to FIGS. 12A and 12B. Fluorescence is emitted in all directions and can also be guided in a specific detection direction by the reflection means described with reference to FIGS. 7A and 7B or the like. To improve the fluorescence detection sensitivity, it is necessary to bring the entrance aperture of the fluorescence spectroscope as close as possible to the detection side of the flow cell 18. However, it is often difficult to place the fluorescence spectroscope near the flow cell 18, because of restrictions on the space or to avoid the effects of heat generated by the fluorescence spectroscope. A fiber bundle 72A or 72B shown in FIG. 12A or 12B can be used as a means for collecting light efficiently. One end of the fiber bundle 72A or 72B is connected to the entrance aperture of the fluorescence spectroscope, and the other end faces a side of the flow cell 18 in its vicinity. FIG. 12A shows the fiber bundle 72A having a rectangular cross section put in place, and FIG. 12B shows the fiber bundle 72B having a circular cross section put in place.

Since the fiber bundle 72A or 72B has a wide light-receiving face, a large amount of light can be collected, and failure to detect fluorescence can be reduced. The loss of light in the optical fiber up to the fluorescence spectroscope can also be reduced. The high flexibility of the optical fiber offers great flexibility in designing the optical path from the flow cell 18 to the fluorescence spectroscope.

Figure 13A:
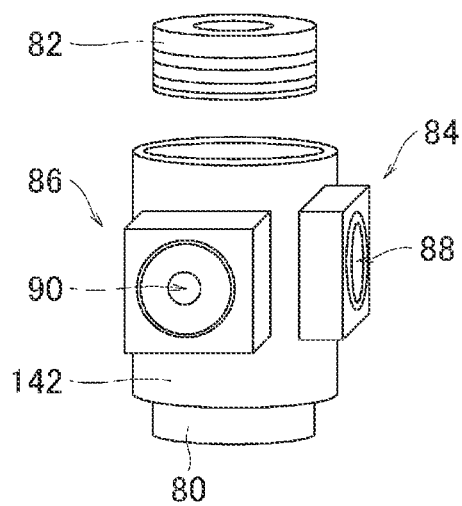
FIGS. 13A and 13B are views illustrating the entire configuration of a flow cell conforming to the High Pressure Gas Safety Act.

A high-pressure fluorescence flow cell 118 will be described as a reference example, with reference to FIGS. 13A and 13B. Due to regulations on the selection of materials used for cell bodies, stipulated by the High Pressure Gas Safety Act in Japan, for example, unlike in the first and second embodiments, a cell body 142 is prevented from being made by a light-transmissive material alone, such as silica glass, in some cases. In that case, the flow cell 118 in this embodiment is useful. In the figures, the cell body 142 of the flow cell 118 is made of a metallic material such as SUS 316, except for attachments such as an incident portion 84 and an output portion 86.

The flow cell 118 includes the cell body 142, an entry-side cell cap 80, an exit-side cell cap 82, the incident portion 84, and the output portion 86. In the cell body 142, an intra-cell flow path 132 that can withstand a pressure of 10 MPa or higher is formed in the Z direction. The entry-side cell cap 80 and the exit-side cell cap 82 are secured to both ends of the intra-cell flow path 132 with gaskets 124 and 126 placed respectively therebetween. As shown in FIG. 13, the exit-side cell cap 82 may have an external thread, and the cell body 142 may have an internal thread, so that the exit-side cell cap 82 can be screwed into the cell body 142. An entry-side flow path and an exit-side flow path of the high-pressure fluid are connected to the cell caps 80 and 82, respectively.

In one feature, the flow cell 118 has a light guiding path 88 for excitation light and a light guiding path 90 for fluorescence at right angles to the central axis of the intra-cell flow path 132. The two light guiding paths 88 and 90 cross each other at right angles and are connected to the intra-cell flow path 132 at the center of the cell body 142. Each of the light guiding paths 88 and 90 has a window plate 92 made of a light-transmissive material such as silica glass to block the path at the middle thereof. The window plate 92 is secured to the cell body 142 by an window-plate holder 94 and isolates the intra-cell flow path 132 from the outside of the flow cell 118.

The excitation light directed to the incident portion 84 travels in the light guiding path 88 formed in the window-plate holder 94 for excitation light, passes through the window plate 92 for excitation light, and reaches the intra-cell flow path 132. In the intra-cell flow path 132, the excitation light strikes the high-pressure fluid perpendicularly to the central axis. Fluorescence from the high-pressure fluid passes through the window plate 92 for fluorescence disposed perpendicularly to the light guiding path 88 of the incident portion 84, travels in the light guiding path 90 formed in the window-plate holder 94 for fluorescence, and exits the flow cell 118.

Figure 13B:
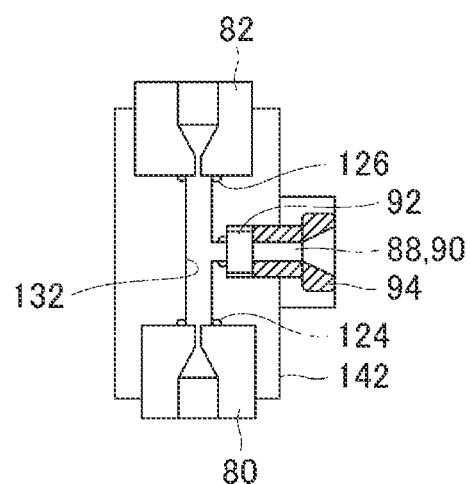

In the cell body 142 shown in FIG. 13B, another light guiding path is not provided in the position opposite to the light guiding path 88 for excitation light, with respect to the intra-cell flow path 132. It is possible that the excitation light entering the intra-cell flow path 132 may scatter and get into the light guiding path 90 for fluorescence. To eliminate the influence of such scattered light, a light guiding path for guiding excitation light to an exit may be disposed in the position opposite to the light guiding path 88 for excitation light, with respect to the intra-cell flow path 132. The light guiding path for guiding excitation light to the exit should be provided such that the central axis thereof is aligned with the central axis of the light guiding path 88. Then, the excitation light entering the intra-cell flow path 132 can be released from the light guiding path for the exit, suppressing the occurrence of scattered light and improving the fluorescence detection sensitivity.

In the high-pressure fluorescence flow cell 118 in this embodiment, the cell body 142 is made of a metallic material such as SUS 316, and just the window plates 92 in the incident portion 84 and the output portion 86 are made of a light-transmissive material such as silica glass. Therefore, this high-pressure fluorescence flow cell 118 has a withstand pressure of 10 MPa or higher and also conform to the regulations stipulated by the High Pressure Gas Safety Act in Japan.

EXAMPLE 1

Improvement in Sensitivity (Comparing Fluorescence Detection with Ultraviolet-visible Absorbance Detection)

Anthracene was injected into the column of a supercritical fluid chromatograph (SFC) under the following separation conditions. Fluorescence detection was carried out by a fluorescence detector according to the present invention, disposed after the column, and a chromatogram was obtained. To detect absorbance of anthracene under the same separation conditions, an ultraviolet-visible absorbance detector was disposed after the column, and a chromatogram was obtained. The obtained chromatograms are shown in FIGS. 14A and 14B. The peak areas, peak heights, and signal-to-noise ratios (S/N ratios) of the chromatograms are listed in Table 1 below. With a conventional SFC, a chromatogram could be obtained just with the ultraviolet-visible absorbance detector. By using the flow cell according to the present invention, a chromatogram can also be obtained with the fluorescence detector. As shown in FIGS. 14A and 14B and Table 1, a peak of anthracene was detected after only 2.5 to 3.0 minutes from the beginning of injection of the sample. The peak height is 245861 μV, which is more than 25 times the peak height obtained with the ultraviolet-visible absorbance detector. The peak area was more than 18 times the one obtained conventionally, and the SiN ratio was more than 54 times the value obtained conventionally. It was thus confirmed that the SFC enables quick analysis and that fluorescence detection improves the detection sensitivity significantly.

Separation Conditions
  $CO_2$: 3 ml/min
  Temperature: 40° C.
  Pressure: 15 MPa
  Column: Silica gel (I.D. 4.6 mm×length 250 mm)
  Injected amount: 5 μl
  Sample: Anthracene 1.1 μg/ml
  Fluorescence detection: 330-nm excitation light, 400-nm fluorescence
  Ultraviolet-visible detection: 240 nm

TABLE 1

|  | FLUORESCENCE DETECTOR | ULTRAVIOLET-VISIBLE ABSORBANCE DETECTOR | RATIOS |
| --- | --- | --- | --- |
| PEAK AREAS | 716360 | 39575 | 18.10 |
| PEAK HEIGHT | 245861 | 9504 | 25.87 |
| S/N RATIOS | 429.4 | 7.9 | 54.35 |

EXAMPLE 2

Microanalysis (Polycyclic Aromatic Hydrocarbon)

Polycyclic aromatic hydrocarbons (PAHs) are highly carcinogenic harmful material contained in exhaust gas and the like and are regulated in many countries. Microanalytical means for analyzing PAHs is strongly demanded. PAHs have strong fluorescence and can be analyzed by fluorescence detection. Therefore, microanalysis of PAHs becomes possible by combining separation by using a supercritical fluid chromatograph (SFC) and fluorescence detection by using a flow cell according to the present invention.

PAHs were injected into the column of a supercritical fluid chromatograph (SFC) under the following separation conditions, and fluorescence of sample constituents separated by the column was detected. The obtained chromatogram is shown in FIG. 15. As shown in the figure, PAHs, formed of many constituents such as naphthalene and fluorene, were separated quickly in the column of the SFC, and the peaks of all the constituents were detected in about 20 minutes by fluorescence detection. A micro flow cell of 0.5 to 50 μl that can be configured using a high-pressure fluorescence flow cell according to the present invention is suitable when a minute amount of sample (such as 5 μl) is injected. As a result, minute amounts of sample constituents were detected as clear peaks.

Separation Conditions
  $CO_2$: 3 ml/min
  Temperature: 40° C.
  Pressure: 20 MPa
  Column: ODS (I.D. 4.6 mm×length 250 mm)
  Injected amount: 5 μl
  Samples: Naphthalene, fluorene, anthracene, phenanthrene, pyrene, 1,2-benzanthracene, triphenylene, chrysene, benzopyrene
  Fluorescence detection: In general fluorescence detection of sample constituents, single-wavelength excitation light is input for each constituent, and single-wavelength fluorescence is measured. The wavelengths of the excitation light and fluorescence depend on the constituents as listed below.
    Naphthalene, fluorene: 270-nm excitation light, 330-nm fluorescence
    Anthracene, phenanthrene: 250-nm excitation light, 370-nm fluorescence
    Pyrene: 335-nm excitation light, 390-nm fluorescence
    Benzanthracene, triphenylene, chrysene: 280-nm excitation light, 380-nm fluorescence
    Benzopyrene: 290-nm excitation light, 440-nm fluorescence

EXAMPLE 3

Precolumn Derivatization

Figure 16:
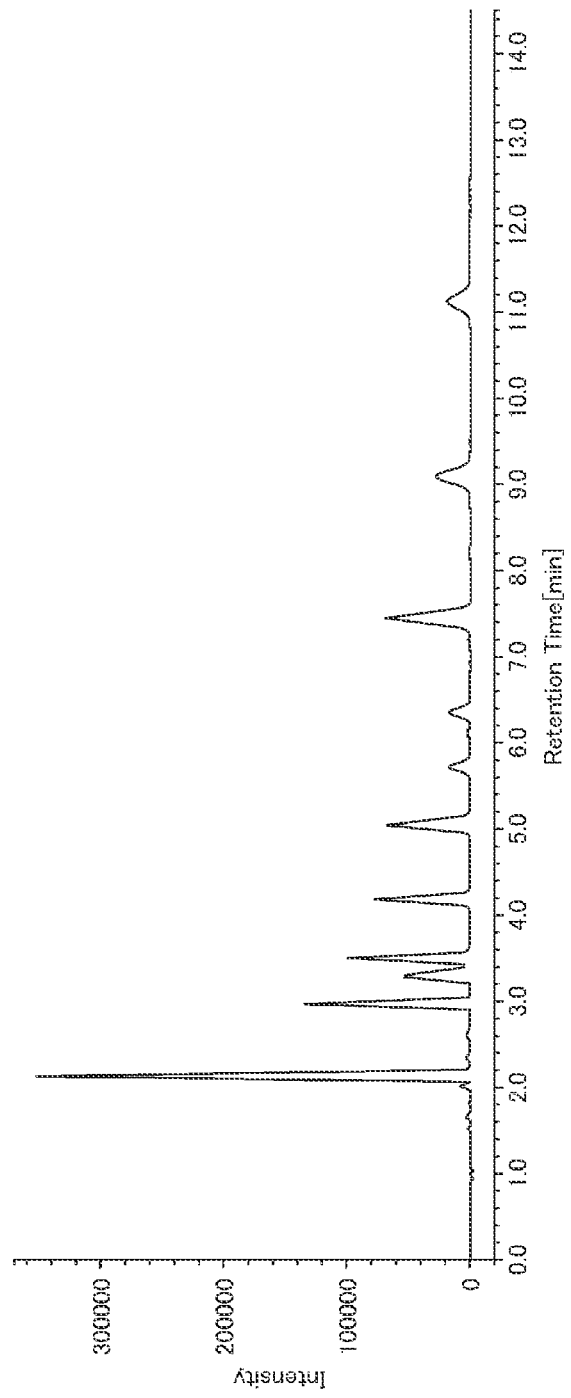
FIG. 16 shows a chromatogram obtained as a result of separation of free fatty acids by precolumn derivatization using the supercritical fluid chromatograph according to the present invention.

Some samples (such as fatty acids) that do not respond sufficiently to the detector can be detected at a sufficient sensitivity after they are converted in a chemical reaction to matter showing a strong response. This technique is referred to as derivatization. FIG. 16 shows results obtained by separating free fatty acids by a supercritical fluid chromatograph (SFC) using the precolumn derivatization under the following separation conditions. To analyze free fatty acids with a conventional SFC, an expensive mass spectrograph is needed. In contrast, an SFC according to the present invention can analyze them with a fluorescence detector. Derivatizazation is an effective method for a variety of samples, including free fatty acids, and can improve the versatility of SFCs.

Separation Conditions
  $CO_2$: 2.8 ml/min
  Acetonitrile: 0.2 ml/min
  Temperature: 40° C.
  Pressure: 15 MPa
  Column: ODS (I.D. 4.6 mm×length 250 mm)
  Injected amount: 5 μl
  Samples: Caprylic acid (C8), Capric acid (C10), Lauric acid (C12), Linolenic acid (C18:3), Myristic acid (C14, Linolenic acid (C18:2), Palmitic acid (C16), Oleic acid (C18:1), Stearic acid (C18), Arachidic acid (C20), Behenic acid (C22)
  Fluorescence detection: 365-nm excitation light, 412-nm fluorescence

DESCRIPTION OF REFERENCE NUMBERS 1,101 Flow cell assembly
2 Light source
4 Excitation light spectroscope
6 Fluorescence spectroscope
7 Photodetector
10 Fluorescence detector
12 shaped holding portion
14 Entry-side flow path
16 Exit-side flow path
18,118 High-pressure fluorescence flow cell
20,120 Entry-side cell holder
22,122 Exit-side cell holder
24,124 Entry-side gasket
26,126 Exit-side gasket
28 Inlet hole
30 Entry-side flow path connection portion
32,132 Intra-cell flow path
34 Outlet hole
36 Exit-side flow-path connection portion
38 Cell holding nut
40 Ring-shaped sheet
42A–42F,142 Cell body
60 Window plate
66 Window-plate holder
68 Exit-side connecting hole
70 Entry-side connecting hole

What is claimed is:

1. A flow cell assembly comprising:
(A) high-pressure flow cell including a cell body made of a light-transmissive material,
wherein the cell body is penetrated by a straight-line flow path for a high-pressure fluid, which allows the high-pressure fluid to be irradiated with excitation light and allows fluorescence of the high-pressure fluid to be detected,
wherein the straight-line flow path is formed in a block that has no fusion parts, and is formed with a cross section of 0.1 mm² to 5 mm², both inclusive, orthogonal to a flow direction of the straight-line flow path,
wherein the ratio t/d of the wall thickness t (mm) to the width d (mm) of the straight-line flow path satisfies formula (1) below, $$\frac{t}{d} \geq \frac{1}{2} \times \left[ \sqrt{\frac{\sigma + P}{\sigma - P}} - 1 \right] \times 1.5 \quad (1)$$

where σ indicates the tensile stress (MPa) of the material of the cell body, and P indicates the withstand pressure (MPa) of the cell body;
(B) an entry-side cell holder that includes an inlet hole for guiding the high-pressure fluid into the high-pressure flow cell, wherein the inlet hole being disposed to be connected to one opening of the straight-line flow path in the high-pressure flow cell;
(C) an exit-side cell holder that includes an outlet hole for outputting the high-pressure fluid from the high-pressure flow cell, wherein the outlet hole being disposed to be connected to the other opening of the straight-line flow path in the high-pressure flow cell;
(D) holding means for holding one of the entry-side cell holder and the exit-side cell holder; and
(E) pressing means for pressing the other of the entry-side cell holder and the exit-side cell holder toward the cell body,
wherein the high-pressure flow cell is held between the pair of cell holders by a pressing force exerted by the pressing means, and a flow path of the flow cell assembly is formed from the inlet hole through the straight-line flow path to the outlet hole,
wherein at least one of the inlet hole and the outlet hole is formed in the same straight line as the straight-line flow path of the cell body, and an end of at least one of the inlet hole and the outlet hole is blocked by a window plate made of a light-transmissive material, and
wherein the cell holder having the window plate has a connecting hole connected to at least one of the inlet hole and the outlet hole in a part inside the window plate; light is able to enter or exit through the window plate in the flow direction of the straight-line flow path; and the high-pressure fluid is able to be input from or output to the outside of the cell holder, through the connecting hole.

2. The flow cell assembly according to claim 1, wherein the ratio of the wall thickness to the width of the straight-line flow path satisfies t/d≥1.8.

3. The flow cell assembly according to claim 1 wherein the straight-line flow path of the cell body is formed by boring a block made of the light-transmissive material or by extending a tube made of the light-transmissive material.

4. The flow cell assembly according to claim 1, further comprising:
a low-friction sheet placed between the pressing means and either of the cell holders.

5. The flow cell assembly according to claim 4, wherein the material of the sheet is a fluorine resin or a polyether ether ketone resin (PEEK).

6. A fluorescence detector comprising:
the flow cell assembly according to claim 1,
an excitation optical system for delivering excitation light into the cell body of the flow cell assembly, and
a light-receiving optical system for receiving fluorescence produced from the high-pressure fluid in the cell body.

7. A supercritical fluid chromatograph which obtains a chromatogram concerning fluorescence by detecting fluorescence of the high-pressure fluid of 10 MPa or higher by using the fluorescence detector according to claim 6.

* * * * *